United States Patent [19]

Nauroth et al.

[11] 4,289,681

[45] Sep. 15, 1981

[54] BORON CONTAINING PRECIPITATED SILICA

[75] Inventors: Peter Nauroth, Wesseling; Robert Kühlmann, Erftstadt; Günter Türk, Hanau, all of Fed. Rep. of Germany

[73] Assignee: Deutsch Gold- und Silber-Scheideanstalt Vormals Roessler, Frankfurt, Fed. Rep. of Germany

[21] Appl. No.: 52,925

[22] Filed: Jun. 28, 1979

[30] Foreign Application Priority Data

Jul. 1, 1978 [DE] Fed. Rep. of Germany ....... 2829045

[51] Int. Cl.³ ............................................. C08L 83/04
[52] U.S. Cl. ............................ 260/37 SB; 106/288 B
[58] Field of Search ................ 260/37 SB; 106/288 B

[56] References Cited

U.S. PATENT DOCUMENTS 3,622,650  11/1971  Berstein et al. ................ 106/288 B

FOREIGN PATENT DOCUMENTS 1154270  9/1963  Fed. Rep. of Germany .
2122066  11/1972 Fed. Rep. of Germany .
2716225  10/1978 Fed. Rep. of Germany .

OTHER PUBLICATIONS

Remy; Lehrbuck der Anorganischen Chemie; vol. 1, p. 400 (1960).
Korda; Aufbereitungstechnik; No. 6, pp. 230–239 (1961).

*Primary Examiner*—Lewis T. Jacobs
*Attorney, Agent, or Firm*—Cushman, Darby & Cushman

[57] ABSTRACT

There is prepared precipitated silica containing boron and having the following physical-chemical data

| | | |
|---|---|---|
| Loss on heating | Weight % | 14–40 |
| pH | | 4–6 |
| Conductivity in 4% aqueous dispersion | /µS | <800 |
| Bulk density | g/l | 130 ± 100 |
| Sieve residue according to Alpine >63/µ | Weight % | <0.1 |
| $SiO_2$ content based on original material | Weight % | 9–76 |
| $B_2O_3$ content based on original material | Weight % | 10–51 |
| $Na_2O$ content based on original material | Weight % | <0.5 |
| $SO_3$ content based on original material | Weight % | <0.8 |

The product is obtained by supplying precipitated silica and ortho boric acid in the ratio of 0.1–3.5:1 continuously to a jet mill and micronizing them together by means of the air of the mill at room temperature.

14 Claims, No Drawings

4,289,681

BORON CONTAINING PRECIPITATED SILICA

BACKGROUND OF THE INVENTION

The invention is directed to a boron containing precipitated silica as well as a process for producing this product.

It is known to produce boron containing silicon dioxide pyrogenically (see Kratel, German OS No. 2122066, the entire disclosure of which is hereby incorporated by reference and relied upon). However, this process of production of the flame hydrolytically recovered boron containing silicon dioxide is very expensive both technologically and industrially so that there has been sought for a long time to employ in its place a wet chemical method produced boron containing silicon dioxide, i.e., a so-called precipitated silica.

According to Nauroth German OS No. 2716225 it is possible to produce a boron containing precipitated silica by adding an aqueous, weakly acid boric acid solution to a washed, nearly electrolyte free precipitated silica filter cake, liquefying this mixture using shearing forces and spray drying, as well as grinding the spray dried product. The entire disclosure of the Nauroth German OS is hereby incorporated by reference and relied upon.

Although the process of production described in the Nauroth German OS No. 2716225 yields a qualitatively highly valuable product without additional expense for apparatus with the carrying out of the spray-drying which is increasingly employed in the preparation of precipitated silica itself, and in which Nauroth process the boric acid is in highly disposed form which is desired for use in polysiloxane-elastomers, there are substantial disadvantages to this process.

Thus, first according to the process of German OS No. 2716225 there can only be recovered boron containing precipitated silica whose $B_2O_3$ content at maximum is 20 weight %. Because of the relatively low water solubility of ortho boric acid (at room temperature 4–6 weight %) after the paste fluidization spray drying process this $B_2O_3$ content only can be attained if the precipitated silica filter cake is treated with large amounts of saturated ortho boric acid solution and there with the spray drying is undertaken from a relatively greatly diluted silica dispersion which unfavorably influences the cost of the drying process. Contents of boric acid of more than 20 weight %, however, also cannot be attained.

Furthermore in the process of German OS No. 2716225 there must be considered that the drying temperatures, particularly the exit dryer temperature of the spray dryer are exactly controlled and regulated since the loss occurring because of the the steam volatility of the ortho boric acid (in this regard, see H. Remy, Lehrbuch der Anorganischen Chemie, Vol. 1, page 400, 11th edition, 1960) leads to fluctuations in the $B_2O_3$ content in the product. Also the ortho boric acid loss can be so high that the process is uneconomical if the temperature of the gases leaving the spray dryer goes above 110°–115° C.

Besides the steam volatile ortho boric acid can get into the free atmosphere with the dryer waste gases or with the inclusion of a so-called scrubber which can be connected downstream to a spray dryer it can get into the operating waste water which is detrimental to the environment.

The problem of the present invention was to develop a product and a process for its production which avoids the mentioned disadvantages.

SUMMARY OF THE INVENTION

An object of the invention is obtained with a boron containing precipitated silica having the following physical-chemical properties (DIN standing for German Industrial Standard).

TABLE H

| | | |
|---|---|---|
| Loss on heating (DIN 55921) | Weight % | 14–40 |
| pH (DIN 53200) | | 4–6 |
| Conductivity in 4% aqueous dispersion | μS | <800 |
| Bulk density (DIN 53194) | g/l | 130 ± 100 |
| Sieve residue according to Alpine <63/μ | Weight % | <0.1 |
| $SiO_2$ contents (DIN 55921) based on original material | Weight % | 9–76 |
| $B_2O_3$ content based on original material | Weight % | 10–51 |
| $Na_2O$ content based on original material | Weight % | <0.5 |
| $SO_3$ content based on original material | Weight % | <0.8 |

In a preferred form of the boron containing precipitated silica the conductivity in 4% aqueous dispersion can be from 100 to 250 μS. In a preferred form the $SO_3$ content and the $Na_2O$ content each are in the range of 0.05 to 0.20%. The $B_2O_3$ content in a preferred form of the invention can be 15 weight %. The $B_2O_3$ content also can be between 25 and 51 weight % or between 28.1 and 51%.

Another object of the invention is a process for the production of boron containing precipitated silica having the physical-chemical properties set forth in Table H above. This process comprises continuously supplying to a jet mill precipitated silica and ortho boric acid in the ratio of 0.1–3.5:1 and micronizing them together by means of the air of the mill.

In this connection there can be added silica having BET surface are of 100–700 $m^2/g$.

In a preferred form of the invention there can also be supplied to the jet grinding unground, spray dried silica.

Thus there can be added, e.g., as unground, spray dried silica a silica having the following physical-chemical properties:

| | | |
|---|---|---|
| Loss on heating (DIN 55921) | Weight % | 2.5–4.5 |
| Loss on drying (DIN 55921) | Weight % | 2.0–7.0 |
| pH (DIN 53200) | | 3.0–7.5 |
| BET surface area (DIN 66131) | $m^2/g$ | 120–180 |
| Bulk density (DIN 53194) | g/l | 200–300 |
| Conductivity in 4% aqueous dispersion | μS | ≦1200 |
| Alpine sieve residue | >0.180 mm: | ≦20 weight % |
| | >0.063 mm: | 50–80 weight % |

Thus there can be added, e.g., as unground, precipitated silica a precipitated silica with the following physical-chemical properties:

| | | |
|---|---|---|
| Loss on heating (DIN 55921) | Weight % | 4.0–6.0 |
| Loss on drying (DIN 55921) | Weight % | 2.0–7.0 |
| pH (DIN 53200) | | 3.5–7.5 |
| BET surface area (DIN 66131) | $M^2/g$ | 400–700 |
| Conductivity in 4% aqueous dispersion | μS | ≦1200 |
| Alpine sieve residue | >0.063 mm: | 20–60 weight % |

-continued

| | | |
|---|---|---|
| >0.180 mm ≦ 20 weight % | | |

In a further illustrative form of the invention there can be added unground, silica-furnace granulate. As unground, precipitated silica-furnace granulate there can be added, e.g. a granulate having the following physical-chemical properties:

| Loss on heating (DIN 55921) | Weight % | 3.5-5.5 |
|---|---|---|
| Loss on drying (DIN 55921) | Weight % | 2.0-7.0 |
| pH (DIN 53200) | | 5.0-7.0 |
| BET surface area (DIN 66131) | m²/g | 150-200 |
| Conductivity in 4% aqueous dispersion | μS | ≦1300 |
| Particle Size | mm | max. 10 |

As the boron containing component there can also be used meta boric acid ($HBO_2$).

According to the invention there can be used all known types of jet mills for the micronization of the precipitated silica-boric acid mixture. In a preferred illustrative form there can be employed a jet mill of the type "Jet-O-Mizer" (see P. Korda "Strahlzerkleinerung und trocknung", in: Aufbereitungstechnik No. 6, pages 230-239 (1961)). In connection therewith, however, attention should be paid that as propellant (or driving) gas there is a steam free medium whose temperature during the jet process also does not increase above 25° C., preferably 20° C. (room temperature). Preferably there is used dry, compressed air. The jet mill conditions such as dosaging speed and dosaging ratio of the two components, precipitated silica and boric acid, amount of mill air, mill air pressure, injector air pressure, amount of injection air, number of nozzles and shape of nozzles are so selected that the fineness of the grinding of boron containing precipitated silica is such that the residue on the 63 microns sieve of an ALPINE air jet sieve is below 0.1 weight %.

Surprisingly it has been proven that precipitated silicas with the micronization of the hygroscopic boric acid at sufficiently large amounts of addition function as grinding aids. Therewith there can be attained by the process of the invention grinding finenesses which cannot be obtained with the spray drying process of German OS No. 2716225 with subsequent normal drying.

Through the jet grinding there is guaranteed that besides an optimum comminution and classification (limiting particle of 63 microns) there takes place an intensive mixing of silica and boric acid. The homogenous distribution of the boric acid in this highly dispersed form has, e.g. for use in polysiloxane elastomers, a great significance since the pure boric acid is present in relatively coarse particle form (250 microns) and its grindability in pure form is difficult.

A further purpose of the invention is the use of the precipitated silica of the invention as filler in compositions based on diorganopoly-siloxanes which are hardenable to elastomers.

Boric acid or its compounds at elevated temperatures cause the condensation of silanol groups. Thus it is known that by heating organopoly-siloxane-boric oxide mixtures to temperatures of 100°-250° C. there can be obtained flowable, elastic materials, so-called silly putty.

Such silly putty which has the unusual property of exhibiting at quick compressive strength elasticity rebound can be produced using the boric acid containing precipitated silica of the invention.

A substantial advantage of the use of the boron containing precipitated silica of the invention as filler in elastomers is that in the production of organopolysiloxane elastomers in the heating to 250° C. and higher in the presence of peroxides boron compounds which can be toxic in volatile form neither evaporate out of the mixtures nor in other ways can diffuse out of the mixture. This advantage is not guaranteed if as boron compounds there are added volatile boron compounds such as alkyl borates, boron hydride, boron hydride-nitrogen compounds, triethanol aminoborate, triisopropanol aminoborate, diphenyl-decaborane, and the like (see Harper German AS No. 1154270 corresponding to U.S. application Ser. No. 696,623 filed Nov. 15, 1957, now U.S. Pat. No. 4,134,194, issued Jan. 16, 1979. The entire disclosure of Harper is hereby incorporated by reference and relied upon).

Illustrative of diorganopolysiloxanes to which the boron containing precipitated silica of the invention can be added as fillers there can be mentioned hydrocarbon and halohydrocarbon substituted polysiloxanes such as diethyl polysiloxane, diisopropyl polysiloxane, dipropyl polysiloxane, methyl phenyl polysiloxane, octadecyl methyl polysiloxane, trifluoropropyl methyl polysiloxane, α,α,α-trifluorotolyl methyl polysiloxane, vinyl methyl polysiloxane, cyclophenyl methyl polysiloxane, ethyl methyl polysiloxane or chloromethyl methyl polysiloxane and mixed polymers for example from dimethyl and diphenyl polysiloxane, dimethyl and methyl vinyl polysiloxane, dimethylphenyl methyl- and methyl vinyl polysiloxane, and dimethyl and tolyl methyl polysiloxane. Many of the diorganopolysiloxanes have the formula $(HO)_x(SiR_y O_{(4-y/2)})_n H$ where R is a univalent hydrocarbyl or halohydrocarbyl group, x has an average of 0.99 to 1.01, y has an average of 1.99 to 2.01, the sum of $x+y$ is 3 and n is a whole number of value of at least 3, usually over 50. In addition to the groups mentioned above R can also be for example cyclohexenyl, methylcyclohenyl, xenyl, benzyl, phenylethyl, phenylpropyl, allyl, cyclopentyl.

When the boron containing precipitated silica of the invention is used as a filler for a diorganopolysiloxane it is usually employed in an amount of 0.5 to 13 parts per 100 parts by weight of diorganopolysiloxane.

A further advantage of the addition of the boron containing precipitated silica in elastomers is in an increased flame resistance of the elastomers.

An additional advantageous area of use of the boron containing precipitated silica of the invention is their use as medium in combatting insects.

The compositions of the invention can comprise, consist essentially of or consist of the materials set forth and the process can comprise, consist essentially of or consist of the steps set forth with such materials.

Unless otherwise indicated all parts and percentages are by weight.

The boron containing precipitated silicas of the invention as well as the processes for producing them and using them are further explained and described in the following examples.

DESCRIPTION OF THE PREFERRED EMBODIMENTS

EXAMPLE 1

There were employed the following products as components for the jet grinding:

An unground, spray dried precipitated silica having the following physical-chemical properties:

| | | |
|---|---|---|
| Loss on heating (DIN 55921) | Weight % | 6.8 |
| Loss on drying (DIN 55921) | Weight % | 3.4 |
| pH (DIN 53200) | | 5.4 |
| BET surface area (DIN 66131) | $m^2/g$ | 162 |
| Bulk density (DIN 53194) | g/l | 245 |
| Conductivity in 4% Aqueous dispersion | $\mu S$ | 490 |
| Alpine sieve residue | >0.180 mm:1 weight % | |
| | >0.063 mm:58 weight % | |

An ortho boric acid (trademark "20 Mule Team" of Deutsche Borax GmbH) having the following properties:

| | | |
|---|---|---|
| Bulk density (DIN 53194) | g/l | 610 |
| Alpine sieve residue | >0.250 mm:traces | |
| | >0.150 mm:7 weight % | |
| | >0.106 mm:27 weight % | |
| | >0.075 mm:44 weight % | |

The precipitated silica was supplied to an air jet mill of the type "Jet-o-mizer 0202" of the firm Fluid Energy Corporation with a velocity of 4.6 kg/h and simultaneously the ortho boric acid with a velocity of 1.4 kg/h. This corresponds to a ratio of silica and ortho boric acid of 3.33:1. The components were supplied to the grinding space by means of an injector which was operated with an injector air pressure of 4.8 bar. There was used dry grinding air pressure of room temperature (20°) and 5 bar. The physical-chemical properties of the silica are set forth in Table 1.

EXAMPLE 2

There were used the following products as components for the air jet mill grinding:

Unground, precipitated silica furnace granulate with the following physical-chemical properties:

| | | |
|---|---|---|
| Loss on heating (DIN 55921) | Weight % | 10.1 |
| Loss on drying (DIN 55921) | Weight % | 5.4 |
| pH (DIN 53200) | | 6.2 |
| BET surface area (DIN 66131) | $m^2/g$ | 169 |
| Conductivity in 4% aqueous dispersion | $\mu S$ | 1210 |
| Particle Size | mm | Max. 3 |

Ortho boric acid as in Example 1.

This precipitated silica-furnace granulate was supplied with a velocity of 3.0 kg/h and the ortho boric acid with the same velocity simultaneously to the air jet mill as described in Example 1. This corresponds to a ratio of precipitated silica to ortho boric acid of 1.00:1. There were chosen the same grinding conditions as in Example 1.

The physical-chemical data of the boron containing precipitated silica are set forth in Table 1.

EXAMPLE 3

There were used the same starting materials as in Example 2. The precipitated silica-furnace granulate was supplied with a velocity of 1.2 kg/h and the ortho boric acid with 4.8 kg/h simultaneously to the air jet mill as described in Example 1. This corresponds to a ratio of precipitated silica to ortho boric acid of 0.25:1. There were chosen the same grinding conditions as in Example 1.

The physical-chemical properties of the boron containing precipitated silica of the invention are set forth in Example 1.

EXAMPLE 4

There were employed the following products as components for the jet grinding:

Unground, precipitated silica with the following physical-chemical properties:

| | | |
|---|---|---|
| Loss on heating (DIN 55921) | Weight % | 8.2 |
| Loss on drying (DIN 55921) | Weight % | 3.0 |
| pH (DIN 53200) | | 7.5 |
| BET surface area (DIN 66131) | $m^2/g$ | 456 |
| Conductivity on 4% aqueous dispersion | $\mu S$ | 340 |
| Alpine sieve residue | >0.063 mm : 30 weight % | |

Ortho boric acid as in Example 1.

The precipitated silica was supplied to the jet mill with a velocity of 3.0 kg/h and simultaneously the ortho boric acid with the same velocity as described in Example 1. This corresponds to a ratio of precipitated silica to ortho boric acid of 1.00:1. There were chosen the same grinding conditions as in Example 1.

The physical-chemical properties of the boron containing precipitated silica of the invention are set forth in Table 1.

EXAMPLE 5

There were chosen the same starting materials as in Example 4. The precipitated silica was supplied with a velocity of 1.2 kg/h, and simultaneously the ortho boric acid with a velocity of 4.8 kg/h to the air jet mill as described in Example 1. This corresponds to a ratio of precipitated silica to ortho boric acid of 0.25:1. There were chosen the same grinding conditions as in Example 1. The physical-chemical properties of the boron containing precipitated silica of the invention are set for in annexed Table 1.

EXAMPLE 6

The same starting materials were chosen as in Example 4. The precipitated silica was supplied with a velocity of 0.6 kg/h and simultaneously the ortho boric acid with a velocity of 5.4 kg/h to the air jet mill as described in Example 1. This corresponds to a ratio of precipitated silica to ortho boric acid of 0.11:1. There were chosen the same grinding conditions as in Example 1.

The physical-chemical properties of the boron containing precipitated silica of the invention are set forth in Table 1.

EXAMPLE 7

The boron containing precipitated silica of the invention of Example 1 is outstanding suitable for the production of silly putty.

For this purpose there was produced in a mixing kneader at room temperature the following mixtures.

| | | |
|---|---|---|
| Dimethyl polysiloxane with terminal Si bound hydroxyl groups (100 cSt) | 200 parts | |
| FeCl$_3$ (anhydrous) | 0.01 parts | |
| Silica according to Example 1 (13.1% B$_2$O$_3$) | 25.9 parts | |

This mixture was warmed for 4 hours at 110° C. in the kneader. After cooling there were mixed 200 parts of the highly viscous boron containing siloxane composition on the rolls with 1 part of oleic acid and 150 parts of Aerosil ® (flame hydrated silica). There were obtained a product having the properties of a silly putty.

There is hereby incorporated by reference the entire disclosure of German priority application No. P 28 29 045.1-41.

TABLE 1

Physical - chemical properties of Boron Containing Precipitated Silicas of the Invention According to Examples 1 to 6:

| Example No. Physical-Chemical Data | 1 | 2 | 3 | 4 | 5 | 6 |
|---|---|---|---|---|---|---|
| SiO$_2$ based on orig. material | 71.0 weight % | 43.9 wgt. % | 17.6 wgt. % | 45.7 wgt. % | 18.3 wgt. % | 9.15 wgt. % |
| B$_2$O$_3$ based on orig. material | 13.1 wgt. % | 28.3 wgt. % | 45.0 wgt. % | 28.1 wgt. % | 45.0 wgt. % | 50.65 wgt. % |
| SO$_3$ based on orig. material | 0.3 wgt. % | 0.6 wgt. % | 0.3 wgt. % | 0.2 wgt. % | 0.1 wgt. % | 0.05 wgt. % |
| Na$_2$O based on orig. material | 0.14 wgt. % | 0.3 wgt. % | 0.1 wgt. % | 0.1 wgt. % | 0.05 wgt. % | 0.03 wgt. % |
| H$_2$O (loss on heating) | 15.4 wgt. % | 26.6 wgt. % | 37.0 wgt. % | 25.9 wgt. % | 36.6 wgt. % | 40.15 wgt. % |
| pH | 5.3 | 4.5 | 4.1 | 5.6 | 4.7 | 4.5 |
| Conductivity | 380 μS | 640 μS | 300 μS | 230 μS | 120 μS | 95 μS |
| Bulk density | 40 g/l | 125 g/l | 215 g/l | 115 g/l | 175 g/l | 220 g/l |
| Sieve residue >63 μmm | <0.1% | >0.1% | >0.1% | >0.1% | >0.1% | >0.1% |

What is claimed is:

1. A boron containing precipitated silica having the following physical-chemical data

| | | |
|---|---|---|
| Loss on heating | Weight % | 14–40 |
| pH | | 4–6 |
| Conductivity in 4% aqueous dispersion | μS | <800 |
| Bulk density | g/l | 130 ± 100 |
| Sieve residue according to Alpine >63μ | Weight % | 0.1 |
| SiO$_2$ content based on original material | Weight % | 9–76 |
| B$_2$O$_3$ content based on original material | Weight % | 10–51 |
| Na$_2$O content based on original material | Weight % | <0.5 |
| SO$_3$ content based on original material | Weight % | <0.8 |

2. A precipitated silica according to claim 1 containing 25–51% B$_2$O$_3$ based on the original material.

3. A precipitated silica according to claim 2 containing 28.1–51% B$_2$O$_3$ based on the original material.

4. A precipitated silica according to claim 1 wherein the weight ratio of SiO$_2$ to B$_2$O$_3$ is from 45.7 to 28.1 to 9.15 to 50.65.

5. A process for the production of the boron containing precipitated silica of claim 1 comprising supplying precipitated silica and ortho boric acid in the ratio of 0.1 to 3.5:1 continuously to a jet mill and micronizing the silica and boric acid together by means of grinding air at about room temperature.

6. A process according to claim 5 wherein the precipitated silica employed has a BET surface area of 100–700 m$^2$/g.

7. A process according to claim 5 wherein there is employed unground, spray dried silica.

8. A process according to claim 5 wherein there is employed unground silica furnace granulate.

9. A process according to claim 5 where there is employed as the boron containing component ortho boric acid.

10. A process according to claim 5 wherein there is employed as the boron containing component meta boric acid.

11. A composition comprising a hardenable elastomeric diorganopolysiloxane containing as a filler the boron containing precipitated silica of claim 1.

12. A composition according to claim 11 wherein the polysiloxane is dimethyl polysiloxane.

13. A composition comprising a hardenable elastomeric diorganopolysiloxane containing as a filler the boron containing precipitated silica of claim 2.

14. A composition comprising a hardenable elastomeric diorganopolysiloxane containing as a filler the boron containing precipitated silica of claim 3.

* * * * *